US006599319B2

United States Patent
Knudsen et al.

(10) Patent No.: US 6,599,319 B2
(45) Date of Patent: Jul. 29, 2003

(54) PROSTHETIC LIGAMENT

(75) Inventors: Robert B. Knudsen, Charlotte, NC (US); Richard E. Nye, Tully, NY (US)

(73) Assignees: Celanese Advanced Materials, Inc., Charlotte, NC (US); Cortland Cable Company, Inc., Cortland, NY (US)

( * ) Notice: Subject to any disclaimer, the term of this patent is extended or adjusted under 35 U.S.C. 154(b) by 0 days.

(21) Appl. No.: 10/017,945

(22) Filed: Dec. 14, 2001

(65) Prior Publication Data

US 2003/0114929 A1 Jun. 19, 2003

(51) Int. Cl.[7] .................................................. A61F 2/08
(52) U.S. Cl. ................. 623/13.11; 623/13.12; 623/13.19
(58) Field of Search ............... 623/13.19, 13.12, 623/13.11, 13.14, 13.2, 13.18

(56) References Cited

U.S. PATENT DOCUMENTS

| 4,917,700 | A | * | 4/1990 | Aikins | ................... 623/13.11 |
| 5,458,601 | A | | 10/1995 | Young, Jr. et al. | |
| 5,575,819 | A | | 11/1996 | Amis | |
| 5,747,137 | A | * | 5/1998 | Cutolo et al. | ................... 428/74 |
| 5,800,543 | A | * | 9/1998 | McLeod et al. | ......... 623/13.11 |
| 5,873,906 | A | * | 2/1999 | Lau et al. | ................... 623/1.15 |
| 5,876,432 | A | * | 3/1999 | Lau et al. | ................... 623/1.15 |
| 6,080,474 | A | * | 6/2000 | Oakley et al. | .............. 428/323 |
| 6,165,210 | A | * | 12/2000 | Lau et al. | ................... 623/1.12 |
| 6,309,423 | B2 | * | 10/2001 | Hayes | ...................... 623/23.75 |
| 6,331,188 | B1 | * | 12/2001 | Lau et al. | ................... 623/1.13 |
| 6,485,819 | B2 | * | 11/2002 | Hayes | ........................ 428/221 |

OTHER PUBLICATIONS

Bolton, C.W. et al, "The GORE–TEX(™) Expanded Polytetrafluoroethylene Prosthetic Ligament," Clinical Orthopaedics and Related Research, 196:202–213, Jun. 1985.

Young, F.A. et al, "Artificial Anterior Cruciate Ligament Research at the Medical University of South Carolina," MUSC Orthopaedic Journal, 3:37–38, Jun. 2000.

* cited by examiner

*Primary Examiner*—David H. Willse
*Assistant Examiner*—Suzette J. Jackson
(74) *Attorney, Agent, or Firm*—Robert H. Hammer, III

(57) ABSTRACT

A prosthetic ligament includes a cord of thermotropic liquid crystal filaments. The cord preferably comprises multifilament thermotropic liquid crystal filaments. The cord has an eye spliced at each of its ends.

10 Claims, 1 Drawing Sheet

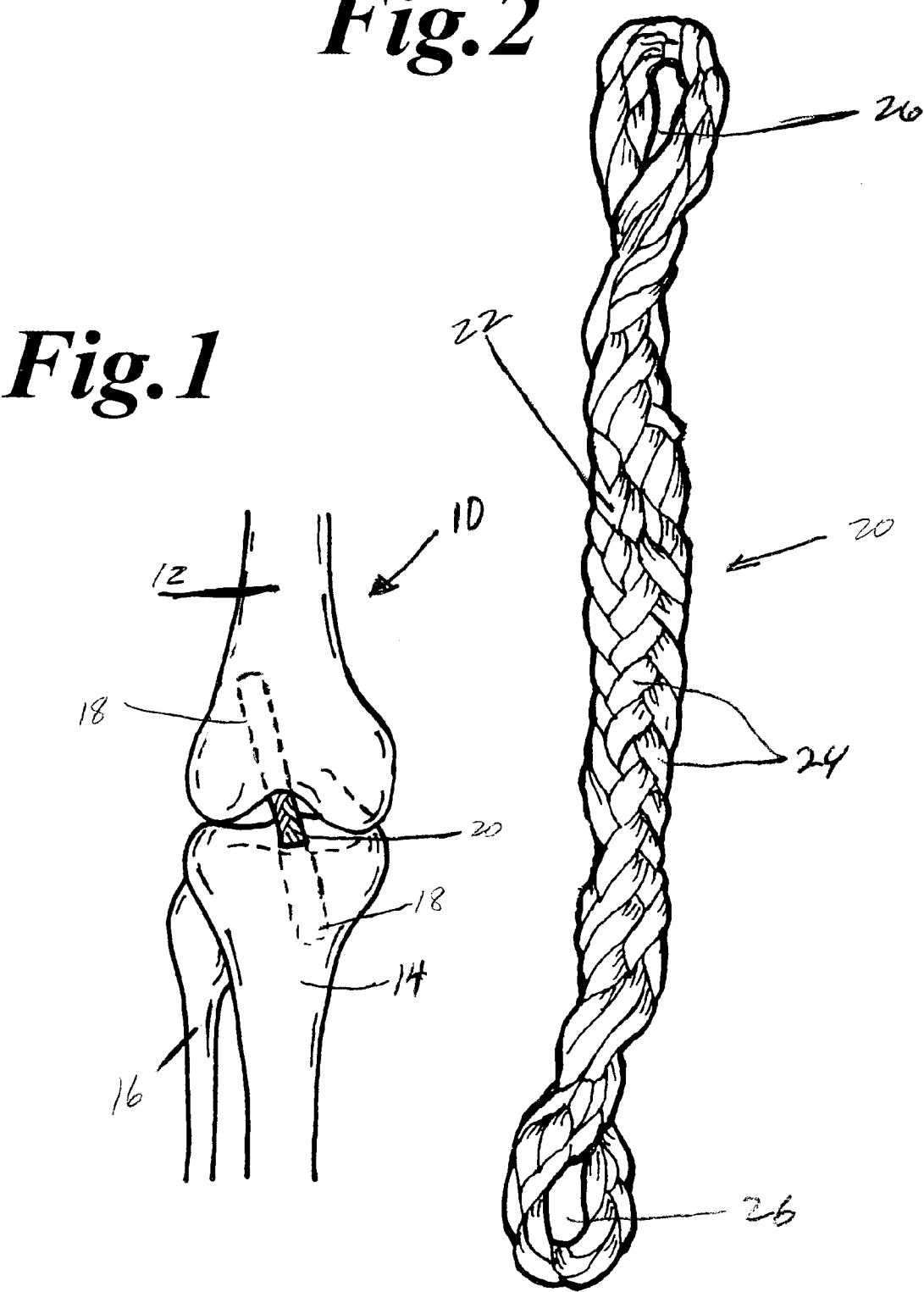

PROSTHETIC LIGAMENT

FIELD OF THE INVENTION

A prosthetic ligament for use in reconstructive surgery is disclosed.

BACKGROUND OF THE INVENTION

A ligament is a band of tissue, usually white and fibrous, that serves to connect bones. For example, the anterior cruciate ligament (ACL) connects the femur to the tibia. A torn ACL is the most common serious ligamentatious injury to the knee joint. Miyasaka, K. et al, "The Incident of Knee Ligament Injuries and the General Population," American Journal of Knee Surgery, 4:3–8, 1991.

Prior attempts have been made to create a suitable prosthetic ligament, but none have received acceptance by the medical community. Those prior attempts include prosthetic ligaments made from: single filament and multi-filament expanded polytetrafluoroethylene (PTFE), see Bolton, C. W. et al, "The GORE-TEX™ Expanded Polytetrafluoroethylene Prosthetic Ligament," *Clinical Orthopaedics and Related Research*, 196:202–213, Jun. 1985; multi-filament polyethylene terephthalate (PET), see U.S. Pat. No. 5,575,819; and lightly or tightly braided polyester filaments, see U.S. Pat. No. 5,800,543. These materials failed because over time the reconstructed knee lost stability that arose from fibril breakage caused by flexing fatigue or rubbing, and/or filament stretching (creep). See Young, F. A. et al, "Artificial Anterior Cruciate Ligament Research At The Medical University Of South Carolina," *MUSC Orthopaedic Journal*, 3:37–38, Jun. 2000.

Accordingly, there is a need for a prosthetic ligament that overcomes the problems described.

SUMMARY OF THE INVENTION

A prosthetic ligament includes a cord of thermotropic liquid crystal filaments. The cord preferably comprises multi-filament thermotropic liquid crystal filaments. The cord has an eye spliced at each of its ends.

DESCRIPTION OF THE DRAWINGS

For the purpose of illustrating the invention, there is shown in the drawings a form of the invention; it being understood, however, that this invention is not limited to the precise arrangements and instrumentalities shown.

FIG. 1 is a schematic illustration of the present invention in use as a prosthetic ligament.

FIG. 2 is an illustration of the present invention.

DESCRIPTION Of THE INVENTION

Referring to the drawings where like numerals indicate like elements, there is shown in FIG. 1 a knee joint 10. Knee joint 10, as shown, consists of the femur 12, the tibia 14, and the fibula 16. Femur 12 and tibia 14 are held together (or stabilized) by prosthetic ligament 20. The terminal ends of ligament 20 are secured to their respective femur 12 and tibia 14 by an anchor 18, shown in phantom. Such anchors are conventional. For example, see U.S. Pat. Nos. 5,458,601, 5,575,819, and 5,800,543, each is incorporated herein by reference. The anchor shown in U.S. Pat. No. 5,458,601 is preferred.

In FIG. 2, prosthetic ligament 20 generally comprises a cord 22, preferably, having eyes 26 spliced therein at each end thereof. Cord 22, preferably, is a string or thin rope made by several strands 24 braided, twisted, or woven together. Cord 22, preferably, consists of a twelve strand braided cord.

Strand 24 comprises a number of filaments, threads, or yarns that are plaited or twisted together to form a unit of the cord 22. Strands 24 are, preferably, made of a multi-filament yarn. The multi-filament yarn is made from filaments having good creep resistance, good flexural strength, and good abrasion resistance. Creep (or delayed deformation) is deformation that is time-dependent and is exhibited by a material subjected to a continuing load. Creep may be measured by tensioning a test sample to a fixed load and periodically recording the tension. A filament with good creep resistance will not show a decrease in tension at 1000 hours (test sample ½" diameter wire-rope of 1500 denier multifilament strands) at over 6000 lbs load). Flexural strength (or flexural fatigue) is a physical property expressed by the number of times a material can be bent on itself through a prescribed angle before it ruptures or loses its ability to recover. Flexural strength may be measured according to ASTM D2176 with a Tinius Olsen/M.I.T. folding endurance tester (400 denier threadlines, 1.36 kg load, oscillated through 270° angle at a rate of 175 cycles/minute). A filament with good flexural strength will show failure above 10,000 cycles-to-failure. Abrasion resistance is the ability of a fiber to withstand surface wear and rubbing. Abrasion resistance may be measured by a rope abrasion test where a test sample (8 strand plain braid 64×1670-dtex threadline, dry test) was bent (over a ½" diameter steel pin at 1.5 cycles/min, 10" stroke, 600 lb load) until failure. A filament (without marine finish) with good abrasion resistance will show failure at over 100 cycles. A preferred filament is a thermotropic liquid crystal polymer filament, commercially available under the trade name VECTRAN® from Celanese Acetate LLC, Charlotte, N.C. The preferred strand is a 2250 denier VECTRAN® yarn having 5 denier per filament (dpf) filaments.

Eyes 26 are adapted to connect ligament 20 to anchors 18. Eyes 26 are, preferably, spliced, in a conventional manner, into cord 22 at its terminal ends. The preferred splicing method is known as the 'locking brummel.' Details of this method are available from Cortland Cable Co., Cortland, N.Y. in a pamphlet, entitled "Fabricating a short splice at the end of a hollow braid," that is incorporated herein by reference.

The present invention may be embodied in other forms without departing from the spirit and essential attributes thereof, and, accordingly, reference should be made to the appended claims, rather than to the foregoing specification as indicating the scope of the invention.

What is claimed is:

1. A prosthetic ligament comprises a prosthetic ligament a cord of thermotropic liquid crystalline filaments, said cord comprising several strands of said filaments.

2. The ligament of claim 1 wherein said cord further comprising twelve braid strand of said filament.

3. The ligament of claim 1 wherein said cord further comprising an eye spliced at each end thereof.

4. The ligament of claim 1 wherein said strands being braided, twisted, or woven together.

5. A prosthetic ligament comprises a prosthetic ligament a cord of braided thermotropic liquid crystalline polymer strands, said cord comprising several strands of said filaments, and the cord having an eye spliced at each end thereof.

6. The ligament of claim 5 wherein said cord further comprises twelve strands.

7. The ligament of claim 5 wherein said strands being braided, twisted, or woven together.

8. A prosthetic ligament comprises a prosthetic ligament being a cord of filaments having a creep resistance of greater than 0% tension loss at 1000 hours, a flexural strength greater than 10,000 cycles-to-failure, and an abrasion resistance greater than 100 cycles-to-failure, and the cord having an eye spliced at each end thereof.

9. The ligament of claim 8 wherein said filaments comprise a thermotropic liquid crystalline polymer.

10. The ligament of claim 8 wherein said cord further comprises twelve strands.

* * * * *